United States Patent
Apostolos et al.

(10) Patent No.: US 8,912,788 B2
(45) Date of Patent: Dec. 16, 2014

(54) LOW POWER STIMULATED EMISSION NUCLEAR QUADRUPOLE RESONANCE DETECTION AT MULTIPLE REFERENCE POWER LEVELS

(71) Applicant: AMI Research & Development, LLC, Windham, NH (US)

(72) Inventors: John T. Apostolos, Lyndeborough, NH (US); Judy Feng, Nashua, NH (US); William Mouyos, Windham, NH (US); Benjamin McMahon, Nottingham, NH (US)

(73) Assignee: AMI Research & Development, LLC, Windham, NH (US)

( * ) Notice: Subject to any disclaimer, the term of this patent is extended or adjusted under 35 U.S.C. 154(b) by 0 days.

(21) Appl. No.: 13/901,765

(22) Filed: May 24, 2013

(65) Prior Publication Data

US 2014/0333302 A1 Nov. 13, 2014

Related U.S. Application Data

(63) Continuation of application No. 13/871,468, filed on Apr. 26, 2013, now abandoned.

(60) Provisional application No. 61/724,384, filed on Nov. 9, 2012, provisional application No. 61/739,282, filed on Dec. 19, 2012.

(51) Int. Cl.
*G01N 27/74* (2006.01)
*G01V 3/00* (2006.01)
*H03F 3/04* (2006.01)

(52) U.S. Cl.
USPC ........... 324/204; 324/307; 324/310; 324/316; 324/318; 330/301

(58) Field of Classification Search
USPC ........................................................ 324/204
See application file for complete search history.

(56) References Cited

U.S. PATENT DOCUMENTS 3,674,998 A * 7/1972 Benz .............................. 702/77
5,122,745 A * 6/1992 Smith et al. ................... 324/307
(Continued)

FOREIGN PATENT DOCUMENTS

JP 2009 264972 A 11/2009
WO WO 2011/094462 A1 8/2011
(Continued)

OTHER PUBLICATIONS

Peshkovsky A. S. et al. "Noise-resilient multi-frequency surface sensor for nuclear quadrupole resonance," Journal of Magnetic Resonance, Academic Press, Orlando, FL, vol. 194, No. 2, Oct. 1, 2008, pp. 222-229.

(Continued)

*Primary Examiner* — Patrick Assouad
*Assistant Examiner* — Christopher McAndrew
(74) *Attorney, Agent, or Firm* — Cesari and McKenna, LLP

(57) ABSTRACT

System and methods for detecting substances such as explosives via the nuclear quadrupole resonance effect. We observe that the nuclear quadrupole resonances of explosives located within a cavity portal involve continuous Rabi transitions which are nonlinear processes since stimulated emission occurs. In other words, where there are no resonances caused by the presence of an explosive, high average power and low average power measurements should be identical. However, when resonances are stimulated by the system, the difference between these two conditions can be compared to determine a correction to measurements made when a person located in the cavity has explosive material on their person, without the need for separate empty portal or elaborate calibration procedures.

12 Claims, 15 Drawing Sheets

(56) References Cited

U.S. PATENT DOCUMENTS

| | | | |
|---|---|---|---|
| 5,986,455 A * | 11/1999 | Magnuson | 324/318 |
| 6,194,898 B1 | 2/2001 | Maguson et al. | |
| 6,246,237 B1 * | 6/2001 | Smith et al. | 324/307 |
| 7,106,058 B2 * | 9/2006 | Wilker et al. | 324/300 |
| 7,109,705 B2 * | 9/2006 | Smith et al. | 324/300 |
| 7,362,182 B2 * | 4/2008 | Barabash et al. | 330/301 |
| 7,564,244 B2 * | 7/2009 | Freytag | 324/318 |
| 7,696,750 B2 | 4/2010 | Fullerton | |
| 2002/0163346 A1 | 11/2002 | Arndt et al. | |
| 2005/0146331 A1 * | 7/2005 | Flexman et al. | 324/318 |
| 2006/0012366 A1 * | 1/2006 | Feldman et al. | 324/310 |
| 2006/0226838 A1 * | 10/2006 | Smith et al. | 324/316 |
| 2006/0255798 A1 | 11/2006 | Crowley et al. | |
| 2007/0182658 A1 | 8/2007 | Ozden | |
| 2007/0211922 A1 | 9/2007 | Crowley et al. | |
| 2009/0167322 A1 * | 7/2009 | Magnuson et al. | 324/642 |
| 2010/0084549 A1 | 4/2010 | Ermakov et al. | |
| 2010/0134292 A1 | 6/2010 | Deavours | |
| 2011/0187363 A1 * | 8/2011 | Zank et al. | 324/307 |
| 2012/0041717 A1 | 2/2012 | Fullerton | |
| 2012/0136585 A1 | 5/2012 | Apostolos | |
| 2012/0139536 A1 | 6/2012 | Zank | |
| 2012/0161761 A1 | 6/2012 | Apostolos | |
| 2012/0161762 A1 | 6/2012 | Zank | |
| 2012/0161771 A1 | 6/2012 | Apostolos | |
| 2013/0234704 A1 * | 9/2013 | Hurlimann et al. | 324/303 |

FOREIGN PATENT DOCUMENTS

| | | |
|---|---|---|
| WO | WO 2011/094463 A1 | 8/2011 |
| WO | WO 2011/094466 A1 | 8/2011 |
| WO | WO 2011/102948 | 8/2011 |
| WO | WO 2011/102948 A1 | 8/2011 |
| WO | WO 2011/126594 A2 | 10/2011 |
| WO | WO 2011/152887 A2 | 12/2011 |

OTHER PUBLICATIONS

International Search Report and Written Opinion, mail date Dec. 20, 2012 for International Application No. PCT/US2012/057425, International Filing Date Sep. 27, 2012, AMI Research & Development, Inc. 15 pages.

Itozaki et al. "Nuclear Quadrupole Resonance for Explosive Detection" Graduate School of Engineering Science, Osaka, 560-8531, Japan, International Journal on Smart Sensing and Intelligent Systems, vol. 1, No. 3, Sep. 2008, pp. 705-715.

Miller, J.B. and Barrall, Geoffrey "Explosives Detection with Nuclear Quadrupole Resonance" *American Scientist*, vol. 93, p. 50-57, 2005.

Bohlen J M et al., "Experimental Aspects of Chirp NMR Spectroscopy," Journal of Magnetic Resonance, Series A, Academic Press, Orlando, FL, vol. 102, No. 3, May 1, 1993, pp. 293-301.

Sauer K. L. et al., "Three-frequency nuclear quadrupole resonance of spin-1 nuclei," Chemical Physics Letters, Elsevier BV, NL, vol. 342, No. 3-4, Jul. 13, 2001, pp. 362-368.

International Search Report and Written Opinion mail date Mar. 28, 2014 for International Application No. PCT/US2013/076020 filed on Dec. 18, 2013 by AMI Research & Development, LLC, 14 pages.

International Search Report and Written Opinion mail date Apr. 2, 2014 for International Application No. PCT/US2013/068683 filed on Nov. 6, 2013 by AMI Research & Development, LLC, 13 pages.

Apostolos et al., "Low-power stimulated emission nuclear quadrupole resonance detection system utilizing Rabi transitions," Proceedings of the SPIE—The International Society for Optical Engineering SPIE—The International Society for Optical Engineering USA, vol. 8709, Jun. 7, 2013, 10 pages.

* cited by examiner

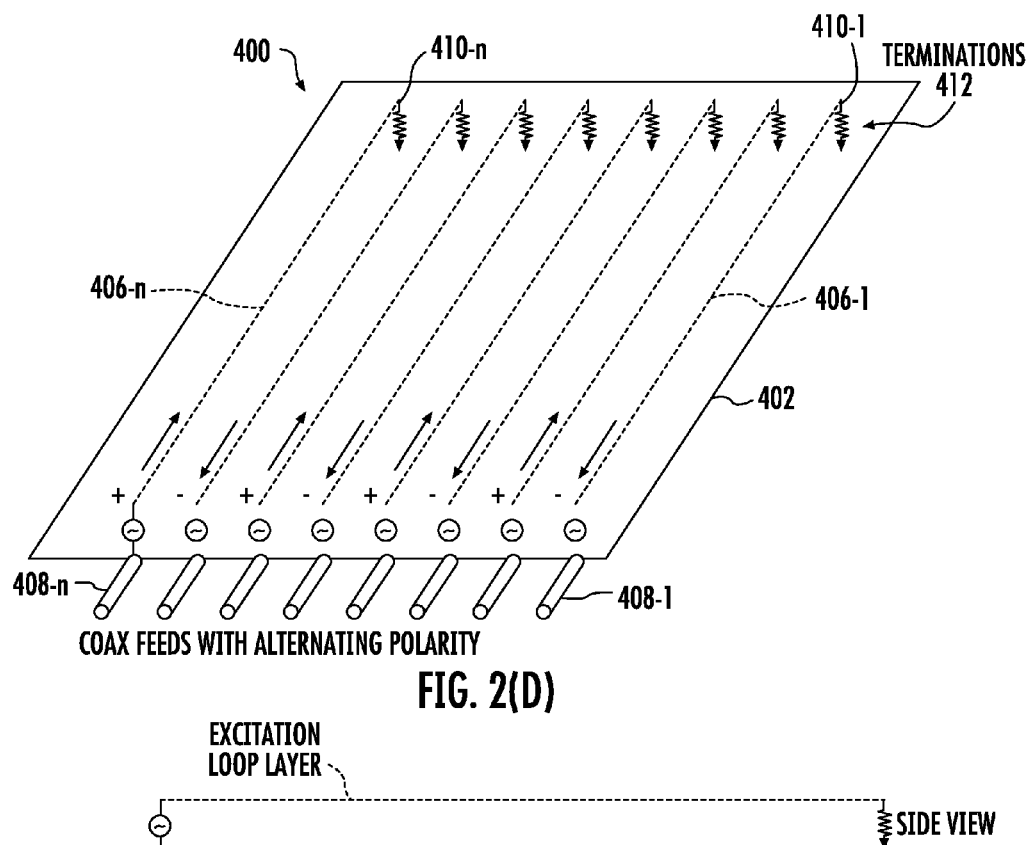

LOW POWER STIMULATED EMISSION NUCLEAR QUADRUPOLE RESONANCE DETECTION AT MULTIPLE REFERENCE POWER LEVELS

CROSS REFERENCE TO RELATED APPLICATIONS

This application is a continuation of commonly assigned copending U.S. patent application Ser. No. 13/871,468, which was filed on Apr. 26, 2013, by John T. Apostolos et al. for a LOW POWER STIMULATED EMISSION NUCLEAR QUADRUPOLE RESONANCE DETECTION AT MULTIPLE REFERENCE POWER LEVELS and claims priority to U.S. Provisional Application No. 61/724,384, filed on Nov. 9, 2012 and U.S. Provisional Application No. 61/739,282 filed on Dec. 19, 2012. The entire teachings of the above applications are incorporated herein by reference.

BACKGROUND

1. Technical Field

This application relates to chemical analysis and more particularly to systems and methods that use nuclear quadrupole resonance.

2. Background Information

It is known that an atom with more than one unpaired nuclear particle (protons or neutrons) will have a charge distribution which results in an electric quadrupole moment. Allowed nuclear energy levels are shifted unequally due to the interaction of the nuclear charge with an electric field gradient supplied by the non-uniform distribution electron density (e.g. from bonding electrons) and/or surrounding ions. This so-called Nuclear Quadrupole Resonance (NQR) effect results when transitions are induced between these nuclear levels by an externally applied radio frequency (RF) field. This electromagnetic field thus induces a magnetic resonance, unique to each material, without using a magnet. A typically NQR detection system consists of a radio frequency (RF) power source, an emitter to produce the electromagnetic excitation field, and a detector circuit which monitors for a RF NQR response coming from the object being analyzed.

NQR has a number of practical uses, such as the detection of land mines, or of narcotics or explosives concealed in luggage, or remote monitoring of fluid levels such as in oil wells.

SUMMARY

Systems that use the NQR effect to detect explosive materials are known in the art; see our co-pending U.S. patent application Ser. No. 12/628,824 filed Sep. 27, 2012 as one example (the entire contents of which are hereby incorporated by reference).

One of the problems with existing explosives detection systems is the need for a stable reference to effect high dynamic range cancellation. An approach is to use a reference signal that is the system response to an empty cavity portal. The response of the system with the explosive and its container in the cavity is then subtracted from the reference. However, the system response to a container with no explosive is not quite equivalent to that of an empty cavity. A more accurate procedure entails using the empty container in the cavity as the reference mode. However, since the "container" in a fielded system is often a human being, it is almost impossible to use the empty container as a reference. This situation is compounded by the fact that the system response for each human being is different.

In pertinent aspects an NQR detection system according to the teachings herein detects Rabi transitions in a material being analyzed. The methodology employs a transmitted waveform with two power state illuminations which are combined to cancel the incident field. The waveform utilized is preferably a continuous linear frequency modulated chirp signal that provides frequency agility, facilitating the use of matched filter detection.

In one embodiment, an enclosed chamber or cavity is used as a detection portal. An accurate detection procedure entails using the "empty container in the cavity" as a reference mode. The solution here is to use the human itself as the reference by taking multiple measurement(s) from the cavity. As a human enters the portal cavity, a first measurement is taken using a relatively low radio frequency power level. A second measurement is then taken at a relatively high power level. The detection system determines a measurement such as by calculating S21 parameters for each measurement. The detected responses to the high and low power emissions should be identical as long as the transfer function of the cavity is not nonlinear. That is, as long as the human being is not carrying a material of interest, the low power and high power measurements should be about the same. However the nuclear quadrupole resonances of materials of interest such as explosives involve continuous Rabi transitions which are nonlinear processes. Thus, when there are such resonances present, the system output for the low and high power excitation can be expected to be different. For example, this difference may be is proportional to the square of the differences in transmittal signal power. That is, when resonances are present, the subtraction should provide an output proportional to the high power measurements squared minus the low power measurement squared.

It is also possible to repeat the human-occupied cavity measurement at a third, still higher power level, which is higher than the second power level. This third power level measurement can then be used to further confirm the presence of explosives.

Additional optional features are appropriate for the system. In particular, analysis has shown the results depend on the frequency of the resonance relative to the start frequency of the transmitted chirp signal. By sequential transmittion of sine and cosine chirped signals and adding the sequential system responses, response detection is improved.

It is furthermore possible to provide components of the radio frequency transmitter that comprise a pair of couplers that derive a reference signal to provide coupling directivity for the signal of interest.

In still other aspects, the response detection process may make use of the fact that there are often three or more expected NQR resonances for certain explosives of interest. These known spectral resonances for various nitrogen-based explosive and nonexplosive materials can be further utilized in the detection of materials of interest.

BRIEF DESCRIPTION OF THE DRAWINGS

The description below refers to the accompanying drawings, of which:

FIGS. 2(d) and 2(e) show another arrangement where a conducting half space layer placed on a floor is used as the portal.

DETAILED DESCRIPTION OF AN ILLUSTRATIVE EMBODIMENT

The preferred solution to the NQR detection problem here is to use the human being (container) as the reference signal by the following procedure:

1) A human enters the portal cavity
2) An NQR measurement is taken using relatively low RF power
3) Another NQR measurement is taken using relatively high RF power For each measurement the system measures a response such as the S21 response. The high and low power measurements are expected be identical as long as the transfer function of the human-occupied portal cavity is not nonlinear.

We observe however, that the nuclear quadrupole resonances of explosives is involve continuous Rabi transitions which are nonlinear processes. In other words, while at NQR resonance the system outputs for the high and low powers are proportional to the square of the input power.

Thus, where there are no resonances present, subtracting the high output from the low output gives zero. With resonances present, this same subtraction gives an output proportional to the squares of the differences in the high and low power measurements.

Figure 1:
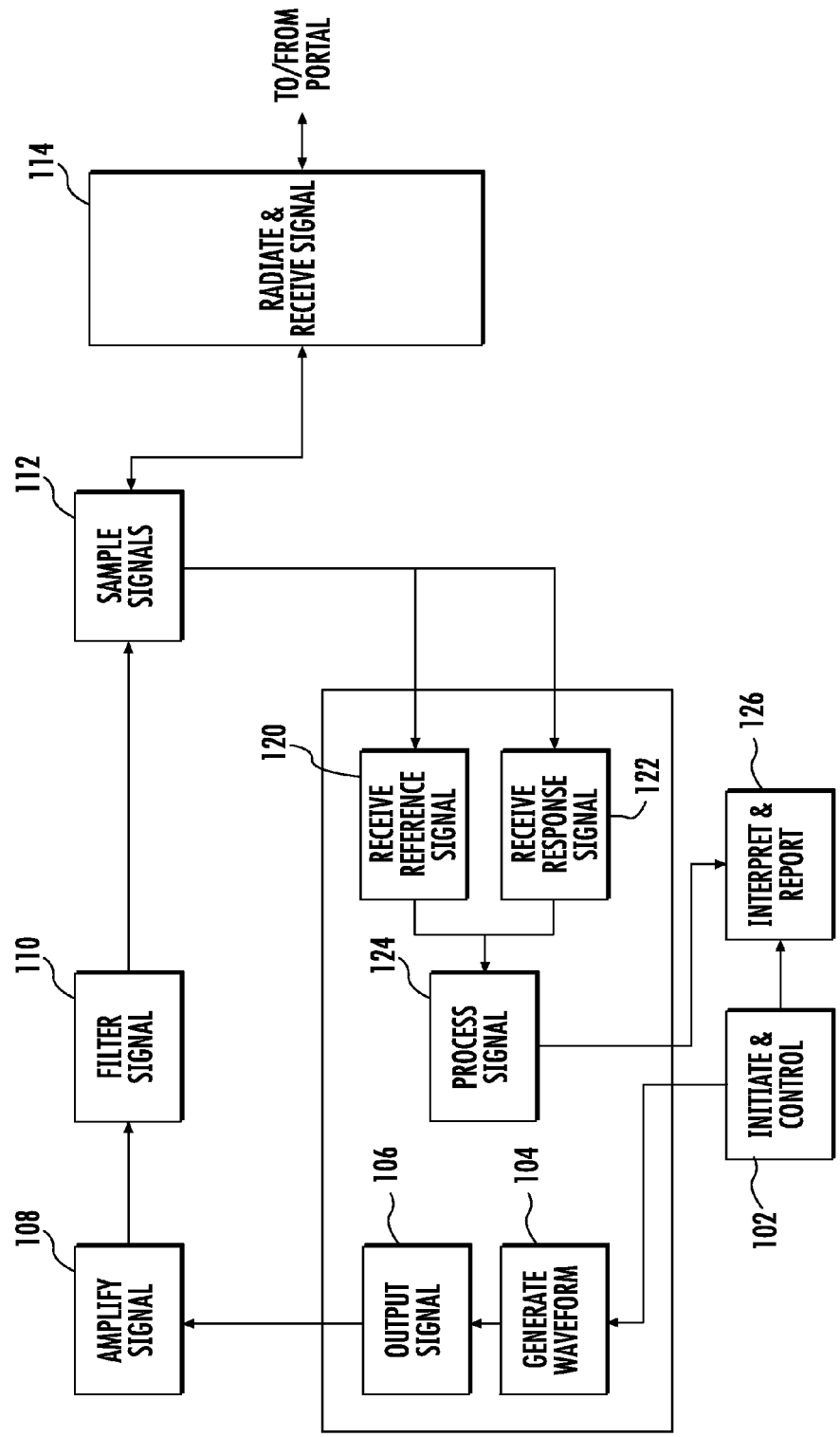
FIG. 1 is a high-level block diagram of an NQR detection system.

FIG. 1 is a high-level diagram of the components of a detection system according to the teachings herein. An initiate and control function 102 may be implemented by a suitable programmable processor. This function controls generation 104 of a suitable transmit waveform which is then produced as an output signal 106. The output signal 106 is amplified 108 and filtered 110. This signal is then sampled 112 prior to it being radiated 114. The radiated signal enters a portal containing the human being of interest. Responses from the portal 114 are then returned to the sampler 112. Both a reference signal 120 and received signal 122 returned from the portal are then fed into signal processing 124. The outputs from signal processing 124 are then interpreted and reported 126.

The detection system of FIG. 1 is typically architected with a combination of digital and RF components. Initialization 102 begins with the transmission of a series of linear chirp waveforms associated with NQR resonance lines of interest. These signals are then amplified 108, filtered 110, and sent to the sensing portal producing a low-power magnetic field. This magnetic field generated in response to the linear chirp is then incident on whatever is contained in the chamber, causing coherent NQR emissions from such contents of the chamber. The response from the chamber contains the transmitted energy, reflected energy, and the NQR signal. To eliminate the transmit signal, samples 112 are taken and used as part of the cancellation algorithm. The response signal is processed by means of a cancellation and matched filter algorithm (via signal portal 124) before being reported 126 as either having an explosive or not.

The inspiration for creating an NQR based detection system with detection times of less than <5.0 seconds stems from the application of continuous wave, chirped signal techniques as typically used in radar applications rather than the pulsed technology which has dominated previous efforts to detect the weak NQR signals. It is well known that when a two (2) state atom is illuminated continuously by an electromagnetic field at resonance, the atom oscillates between state 1 and state 2, alternately absorbing energy from the incident field and emitting coherent energy via stimulated emission as a result of the chirp signal. This process is an attractive way to increase the NQR signal to higher levels.

A transmitter may be operated continuously rather than pulsed if the strong transmitted signal can be separated from the weak signal of interest. A combination of cancellation of the transmitted chirp signal at the receiver and use of directional couplers or circulators are sufficient.

To develop enough cancellation to deal with NQR signals at levels of less than −70 dBm buried in an incident field of 40 dBm, a combination of directional couplers and a two (2) channel base band digital receiver (120, 122) is utilized. The cancellation methodology employs a chirp waveform with alternating two (2) power state illuminations which are combined to cancel the incident field. Since the frequency range of interest covered is 330 KHz to 5 MHz, a stable, wideband Faraday chamber (which we also call a "cavity" or a "portal" herein) to detect the explosives of interest while maintaining a low return loss (>35 dB) over the bandwidth is important for the cancellation methodology to work well.

The waveform utilized is a continuous linear frequency modulated (FM) chirp to provide frequency agility and facilitate the use of a matched filter (124) for the NQR response to the chirp. The transmitter should generate fields that are in the 10 W/m$^2$ range with low leakage beyond the cavity chamber.

Figures 2A, 2B, 2C:
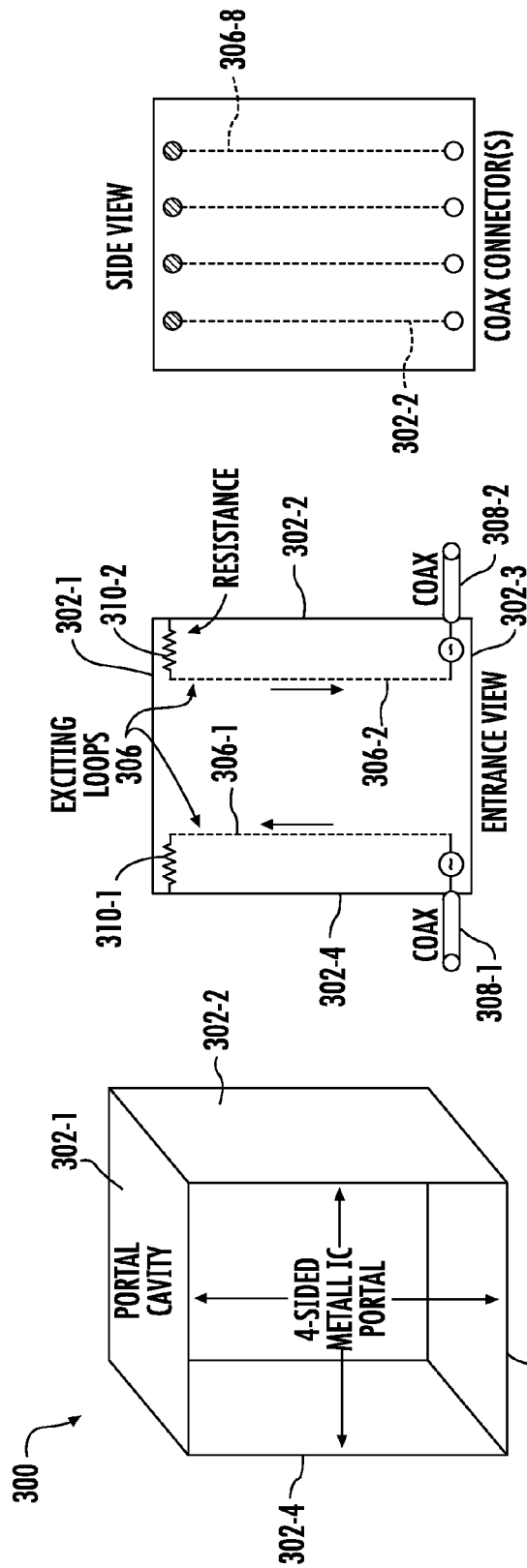
FIGS. 2(a), 2(b) and 2(c) are an example cavity portal that may be used with the detection system described herein.

FIGS. 2(a), 2(b) and 2(c) are an isometric, front and side view of a typical portal cavity (also referred to as the "chamber" herein). In a practical implementation, one or more conductive surfaces are arranged to define a space that is to be monitored such as for access control. This cavity type portal uses a generally rectangular space 300 defined by four conductive walls 302-1, 302-2, 302-3, 302-4. Two or more wire loops 306-1, 306-2 are disposed within the space, typically adjacent selected ones of the conductive surfaces 302. The wire loops 306 are each individually electrically terminated through a resistance 310 to the respective conductive wall(s) in this arrangement. A coaxial cable connector 308-1, 308-2 provides connection to the radio frequency (RF) transmitter and receiver. The conductive walls 302 define the space within which a uniform electromagnetic field can be maintained by the wire loop radiators while at the same time protecting the space from outside disturbances.

Other arrangements are possible for the wire loops. For example, they can be implemented as a balanced transmission line driving two wire segments through a balun with the two segments having a resistance disposed at their mid-point.

In another arrangement, the space to be monitored is defined as a conductive half-space such as defined by a metal surface embedded in a floor. In this other arrangement shown in FIGS. 2(d) and 2(e), the portal space to be monitored is defined as a conductive half-space 410. A system of wire loops 410 provides excitation to such a conductive half space 400, defined by a metal surface 402 embedded in a floor, as shown. The half space 400 can thus be a corridor or large open public area. In the illustration of FIGS. 4(d) and 4(e), the loops 410 are individually fed by coax feeds 408, and terminated by resistors 412. The coax feeds 408 may have alternating polarities, as shown. The excitation loop(s) layer and the conducting half space layer can comprise a composite flexible carpet, in one example. Other arrangements for the space to be monitored are possible.

The portal thus serves two functions—it is both the signal transmission device and the signal sensing device. A low-power magnetic field is generated within the portal cavity and the reflection is received. Some key performance parameters of the portal cavity design included the uniformity of the magnetic field while maintaining acceptable field strength within the cavity, minimal magnetic and electric fields external to the cavity and a cavity sized so that a handicap person can pass through without being impeded.

Simulated results of the detection cavity such as in FIG. 2(a)-2(c) assumed 10.0 Watts of power is applied at a frequency of 5.0 MHz. The power level in the cavity is significantly less than that of the OSHA standard for human safety levels, 100.0 W/m2 for 6.0 minutes.

The uniformity of the magnetic field within the cavity should allow for a body and/or material of interest to be uniformly illuminated within the magnetic field. The low-level magnetic field and electric field external to the cavity, ensure external noise effects are at a minimum where the magnetic field external to the cavity diminishes more rapidly than that of the electric field external to the cavity. To accommodate the majority of travelers and handicap individuals, we prefer a cavity with an opening or walkthrough portion dimensioned at 7.0 feet in height by 3.0 feet in width and 4.0 feet in depth.

Figure 3:
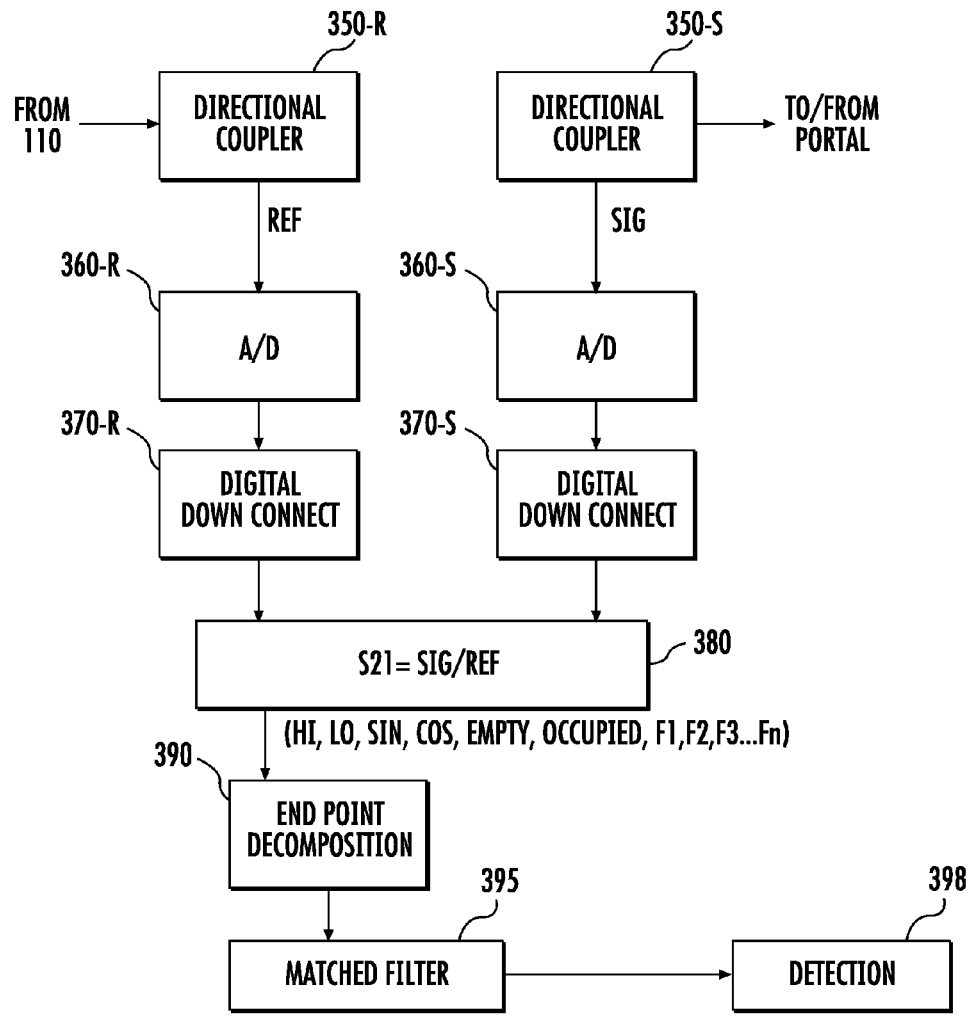
FIG. 3 is a more detailed block diagram of components of the received signal processing.

FIG. 3 contains a more detailed flow diagram of the signal processing 124 components of the system of FIG. 1. These include functions provided by the sample signals function 112, the receive reference signal 120, received signal 122, and the process signal 124. Here a pair of directional couplers 350-R, 350-S feed a corresponding pair of analog-to-digital converters 360-R, 360-S and digital down converters 370-R, 370-S. The signal chains provide a reference signal output (REF) and received signal (SIG) output. A signal measurement block 380 then compares the signal (SIG) to the reference (REF) and provides an initial output. According to the teachings herein, the system is operated at a high power level, a low power level, with both a sine and cosine of the illuminating chirp signal, with the cavity empty and occupied, and with a number of different frequency chirps (covering F1, F2, F3, . . . FN). These outputs are then fed to an end point decomposition block 390 and matched filter 395 prior to a detection process 398.

Figure 4:
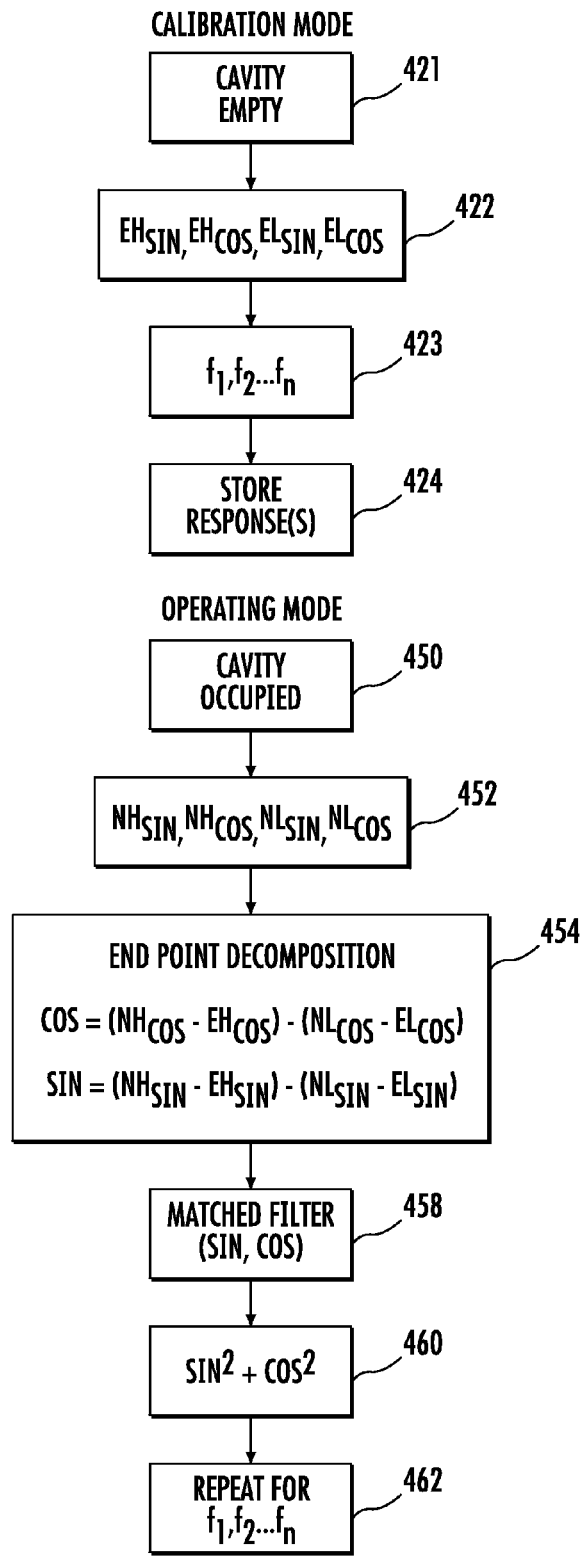
FIG. 4 is a flow diagram of process steps that may be performed by a controller to operate the system in a calibration mode and in an operating mode.

The receive processing is described in more detail in FIG. 4. In a calibration mode, with the cavity empty (step 421), the sequences chirp signals are applied (step 422). A first chirp is emitted into an empty cavity at a relatively low power level with sine phase to the chirp ($EN_{sin}$). Next, a high power sine signal is applied to the empty cavity and the response is measured ($EH_{sin}$). Next, a relatively low power level cosine signal is applied to the empty cavity and the response ($EL_{cos}$) is stored. The same is done for a high power cosine ($EH_{cos}$). These the responses to these chirps are then detected for the frequencies (step 423) of interest and stored (step 424).

An operating mode is then enabled (step 450). The cavity becomes occupied such as with a human being. A set of measurements is taken at low and high power levels each for both the sin and cosine chirps at each frequency of interest (step 452). Next, an end point decomposition process is applied (step 454) to both the sine and cosine responses. A difference is taken between the occupied and unoccupied responses from both the high power and low power responses for each of the sine and cosine chirps. The sine and cosine responses are then applied to a matched filter (step 458). The matched filter contains an ideal expected response for each of the sine and cosine chirps. The results of the matched filter output are then subjected to a magnitude operation such as may be determined by squaring the sine and cosine responses (step 460) and taking this sum. This process is then repeated for the each frequency of interest (step 462).

Figure 5:
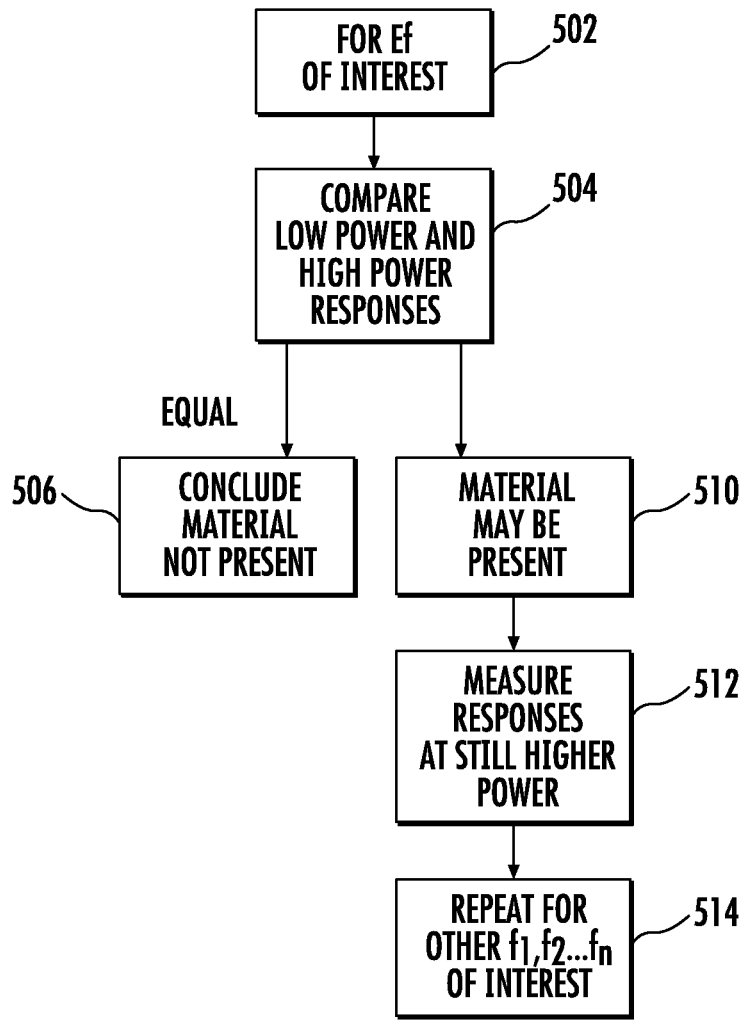
FIG. 5 is a flow diagram of a detection process where low power and high power measured responses are compared.

FIG. 5 shows the process being repeated for each frequency of interest 502. Specifically, the low power and high power responses are compared 504 for each is frequency that may be characteristic of a material of interest. If the responses are relatively equal, a conclusion is reached at 506 that the explosive material of interest is not present. However if the responses are not equal at step 510 such when the high power response contains more energy than the low power response, it is possible that a resonance of interest may be present at that frequency. At this point in step 510 it may be concluded that there is a positive result. Alternatively, a still higher power may be presented at step 512 to the cavity and subjected to the same sine and cosine chirped end point decomposition and matched filter processing. The magnitude of that still higher power measurement may confirm in step 514 that the resonance of interest is present at the designated frequency.

One of the problems noticed with other systems is the measurement to measurement variability of the results. Analysis has shown that the results depend critically on the frequency of the resonance relative to the start frequency of the chirp. In fact the result depends upon the term cosine (arg), where (arg) is proportional to the frequency differences. By using sine and cosine chirps sequentially and adding the sequential outputs in quadrature, the analytic signal is better captured.

Figure 7:
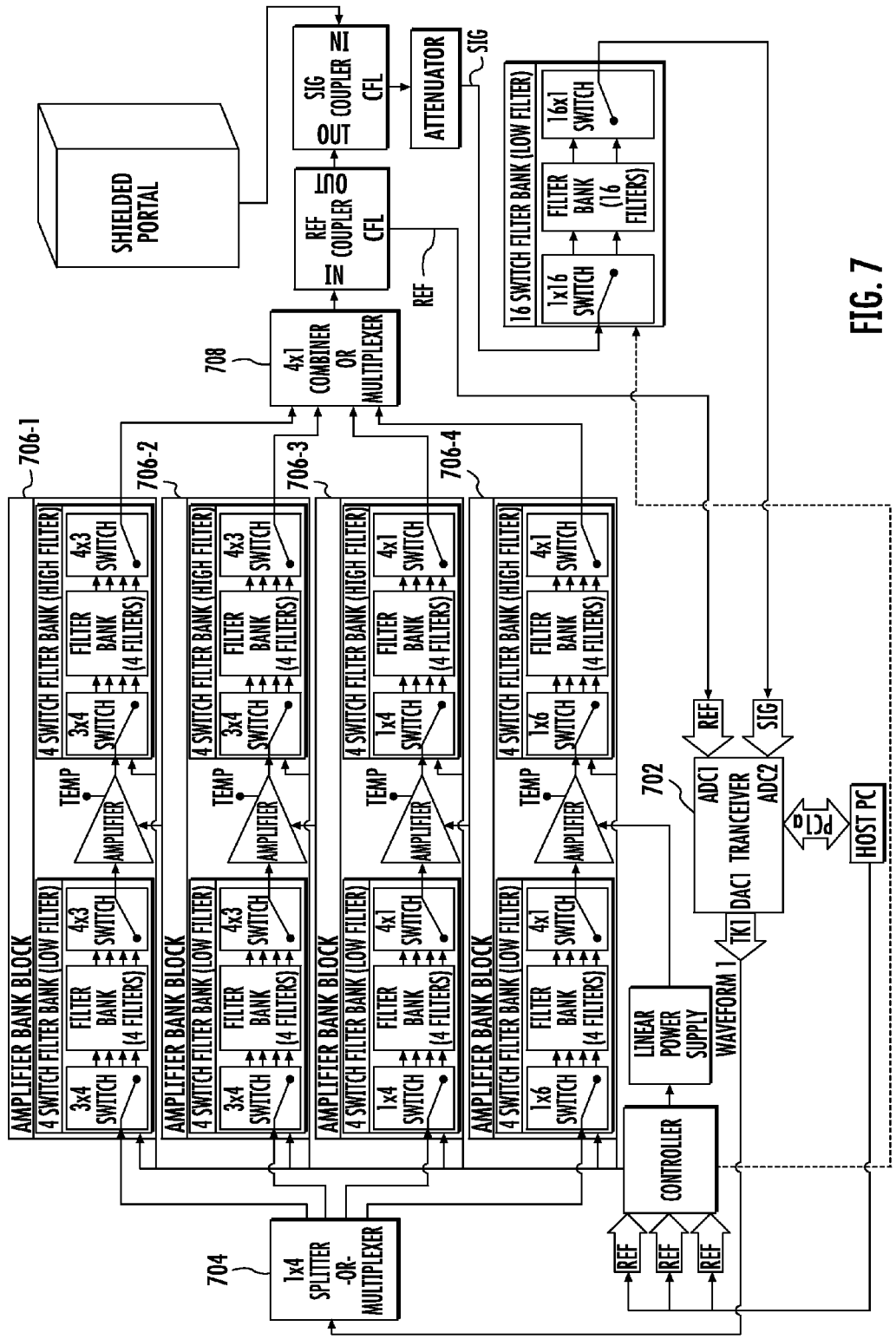
FIG. 7 is architecture using a single DAC and four amplifiers.

A 1-DAC, 4-Amplifier system architecture for testing sixteen (16) nuclear quadrupole resonances is shown in FIG. 7, where a sweep consists of four (4) runs: 1) Sine, 2) Cosine, 3) High Power and 4) Low Power. Four (4) sweeps and thus a total of sixteen (16) runs are necessary to cover the sixteen (16) nuclear quadrupole resonant frequencies of interest.

In this arrangement, a single waveform containing four (4) chirps of varying frequencies is output through the transmit port of the transceiver 702 and split via a 4-way multiplexer or splitter 704. The four (4) signals are then simultaneously sent through four (4) 4-switch amplifier/filter bank blocks 706-1, 706-2, 706-3, 706-4 in parallel so that each of the paths handles one (1) of the four (4) chirps of varying frequency. The four (4) filtered and amplified signals are then 4-way combined or multiplexed 708 and sent through the remaining RF chain, where the two (2) final inputs to the transceiver are the REF and SIG signals. As explained above, the REF signal is a reference signal sampled from the system in order to account for any anomalies the system may incur per run. The SIG signal is the signal sampled from the shielded portal.

Figure 8:
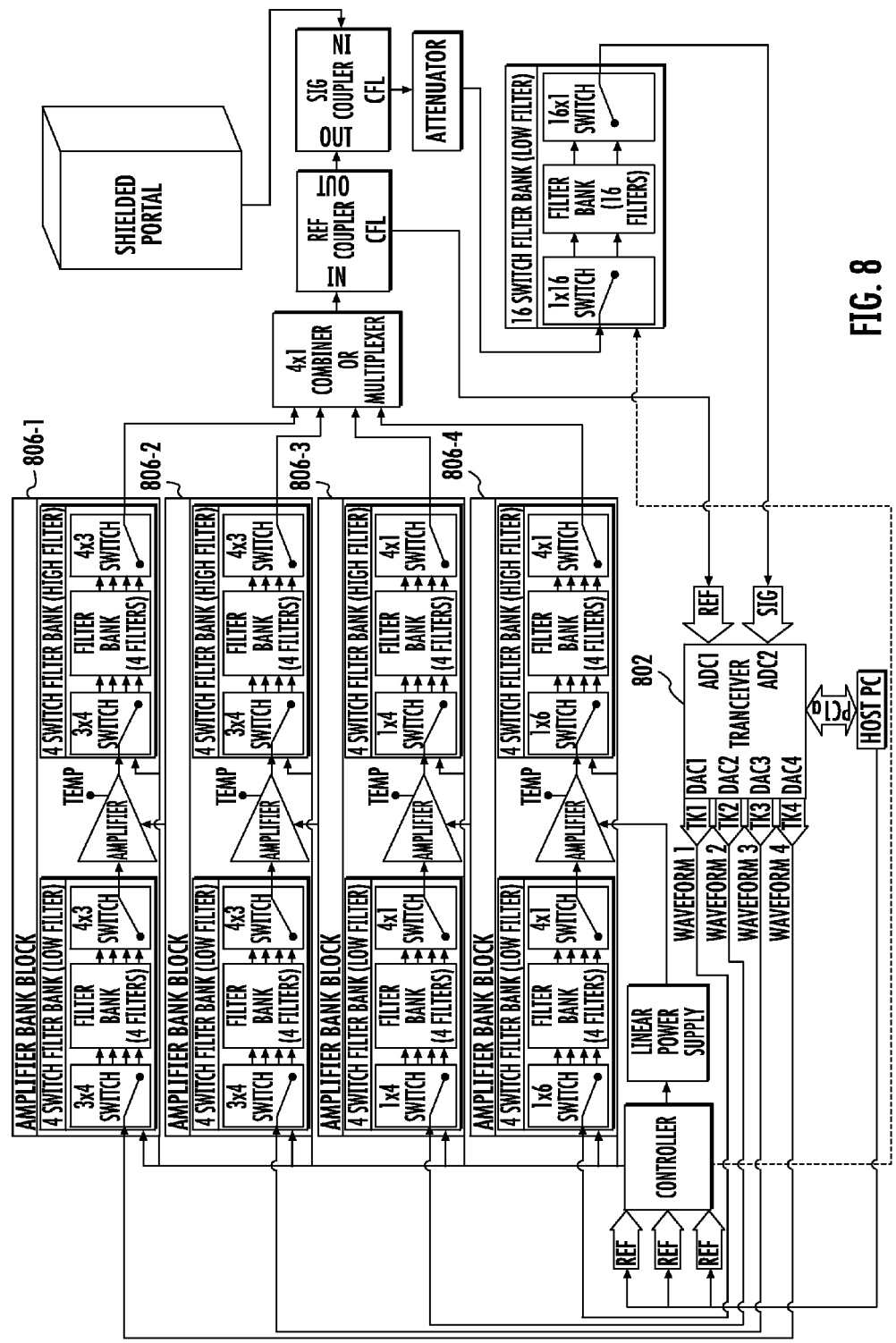
FIG. 8 is an architecture using four DACs and four amplifiers.

An alternative to the 1-DAC, 4-Amplifier system architecture is the 4-DAC, 4-Amplifier system architecture shown in FIG. 8. In this embodiment, a single transceiver 802 with four (4) parallel transmit ports each handle a single waveform containing only one (1) chirp. This transceiver architecture eliminates the need for a 4-way multiplexer or splitter at the input of the four (4) amplifier/filter bank blocks and simplifies the waveform output from the transmit port. The remainder of the system architecture from the amplifier/filter bank blocks 806-1, 806-2, 806-3, 806-4 on is identical to that of the 1-DAC, 4-Amplifier system architecture of FIG. 7.

Figure 6:
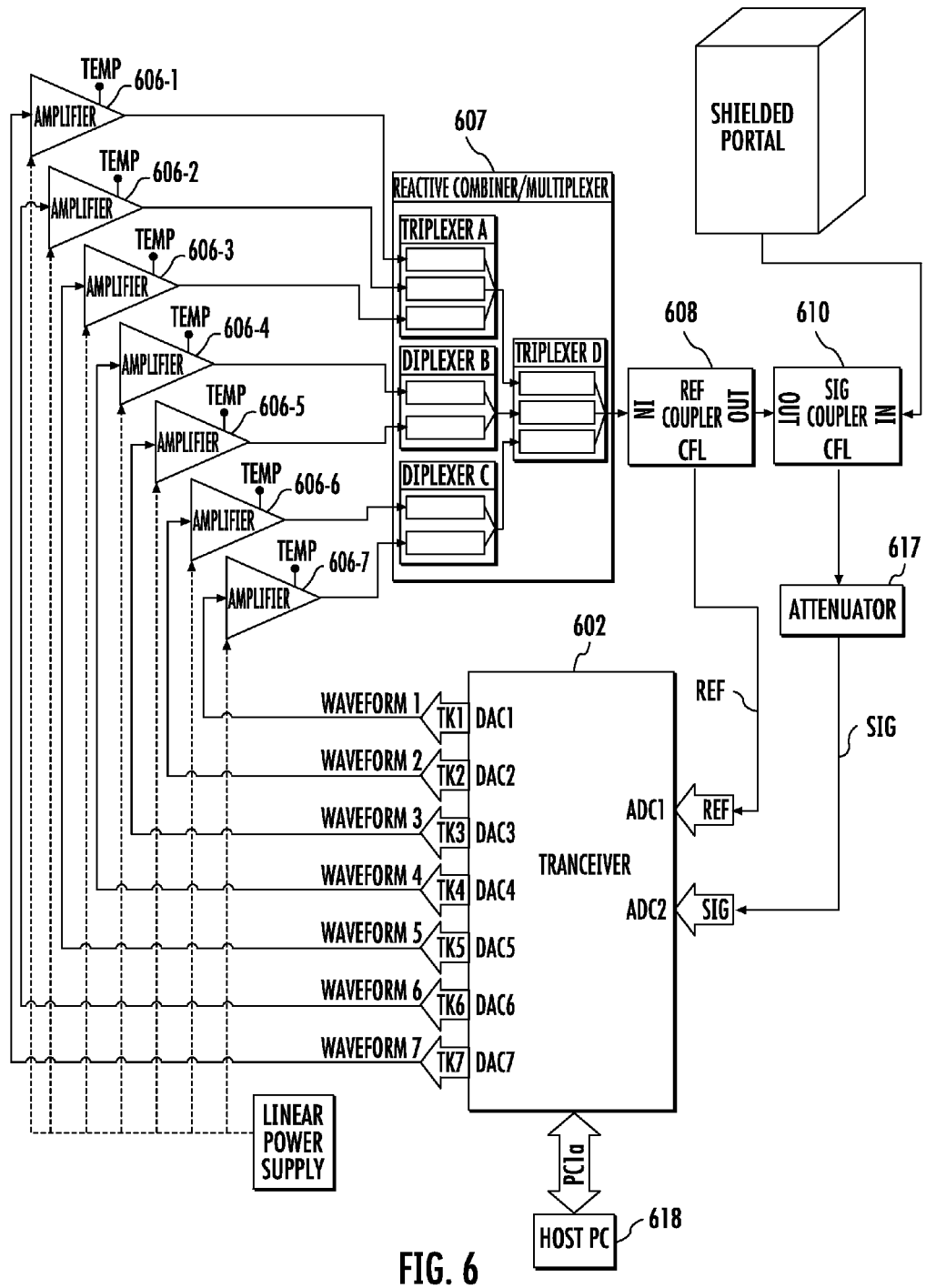
FIG. 6 is a system architecture using seven amplifiers and seven digital to analog converters (DACs).

The architectural implementation for the case where five (5) materials are of interest and only one (1) resonance per material can be sampled at a time is the 7-DAC, 7-Amplifier System Architecture shown in FIG. 6. In this embodiment, a transceiver 602 with seven (7) parallel transmit ports and corresponding seven (7) amplifiers (606-1, . . . , 606-7) are necessary due to frequency band breaks where each transmit port handles a single waveform containing only one (1) chirp. This transceiver architecture gets rid of the need for a splitter at the input of the amplifier and simplifies the waveform output from the transmit port so that only a single signal waveform is needed per port. The need for filter banks at the inputs and outputs of the amplifiers is unnecessary in this architecture since the reactive combiner/multiplexer at the output of the amplifiers serves as a filtering component for each signal in addition to serving as a low-loss combiner. The combined signals at the output of the reactive combiner/multiplexer 607 (which may include a set of duplexers and triplexers) are sent through the remaining RF chain consisting of two (2) couplers 608, 610 and a shielded portal, where eventually the two (2) final inputs to the transceiver are the REF and SIG signals which come from the two (2) coupled ports of the two (2) couplers. The REF signal is a reference signal sampled from the system in order to account for any anomalies the system may incur per run. The SIG signal is the signal sampled from the shielded portal.

Key components of the RF chain are the two (2) directional couplers that are associated with the REF and SIG signal ports which provide coupling and directivity necessary for the signal of interest to be sampled properly. The linearity of these couplers is paramount due to the nature of the high and low power methodology where any non-linearity in the system can cause error in the results. In order to ensure linear coupling, the use of ferrites is not desired due to intermodulation or distortion which can ensue if high enough power is applied. A lumped component approach [1] is one way of implementing a linear no-ferrite coupler. Additional sections can be added for additional bandwidth, more flatness and more directivity. See K. Wincza and Z. Grusczynski, "Miniaturized Quasi-Lumped Coupled-Line Single-Section and Multisection Directional Couplers," IEEE Trans. Microw. Theory Tech., vol. 58, no. 11, pp. 2924-2931, November 2010 for examples of suitable couplers.

Experimental results showed an average signal to noise ratio of better than 10.0 dB for quantities of several hundred grams of explosives material. In the experiments, three (3) resonances of each explosive were searched for. A tri-modal fusion algorithm was employed using the three (3) resonances.

Figure 9:
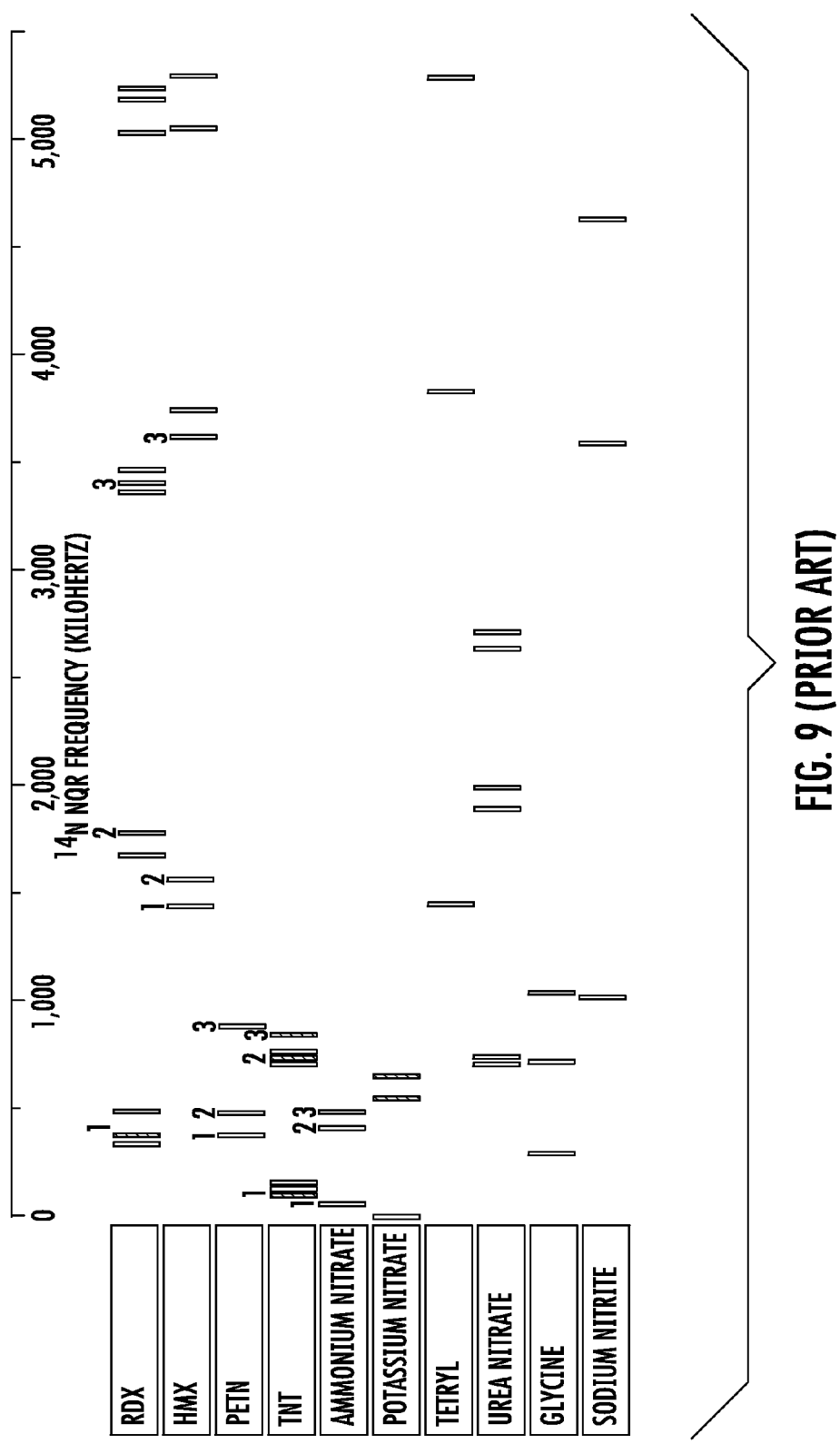
FIG. 9 is a expected spectral response of NQR resonance lines for various materials.

The published spectrum of NQR resonance lines for various nitrogen based explosive and non-explosive materials is shown in FIG. 9. This chart was used to identify three (3) resonance lines of interest for each material in the experiments, where the numerical designation above each material resonance line correspond to the resonance frequencies of interest and/or the group of resonances of interest, as is the case for RDX and TNT.

The matched filters (see FIG. 3) have a resolution bandwidth of approximately 10.0 KHz with an accuracy of 2.0 KHz. These filters do not use all the information available in the NQR response and it is anticipated that resolution bandwidths below 5.0 KHz should be possible. Wideband local manmade noise is most likely the main source of interference in the NQR frequency range. A coherent integration time of, say, 0.2 seconds should help mitigate any interference. Along with the shielded portal, the FM chirp waveform provides a certain amount of noise immunity since the NQR signals are modulated by the FM sine and cosine chirp waveform and the process of de-chirping is actually a first stage matched filter with a large time bandwidth product.

A series of experiment tests were conducted utilizing our system to validate our approach. The tests verifying theoretical calculations were performed for the following explosive materials: ANFO, HMX, PETN, RDX and TNT. Many of the aforementioned explosive materials were commercially available only as mixtures and not in their pure form. Table 1 shows the list of commercial explosives that were tested, the breakdown of which pure explosive material is within each commercial explosive and the associated amounts of each material.

TABLE 1

Table of Measured Explosives and Quantities.

| # | Commercial Packaged Form | Commercial Explosive Name | Explosive Material | | Explosive Quantity |
|---|---|---|---|---|---|
| 1 | 5 GAL Bucket | Austinite | 100% | ANFO | 5 kg |
| 2 | 1000 ft Roll | Shock Tubing | 100% | HMX | 300 grams |
| 3 | 2000 ft Roll | Detonating Cord | 100% | PETN | 600 grams |
| 4 | 70 Caps in a Box | Non-Electric Detonators (in Metal Shell) | 50% | PETN | 226 grams |
|   |   |   | 50% | RDX | 226 grams |
| 5 | 50 Lbs in a Box of 100 Boosters | Cast Boosters | 50% | TNT | 450 grams |
|   |   |   | 16.67% | PETN | 150 grams |
|   |   |   | 16.67% | RDX | 150 grams |
|   |   |   | 16.67% | HMX | 150 grams |

Each of the commercial explosives in their packaged form was tested using a detection system where the input linear chirp waveforms associated with NQR resonances of each of the explosive materials was employed and 6.0 Watts of power applied to the wideband Faraday chamber. The measured results from this series of tests for the five (5) listed commercial explosives from Table 1 are shown in FIGS. 10-13 with the cancellation and matched filter algorithm applied.

Figure 10:
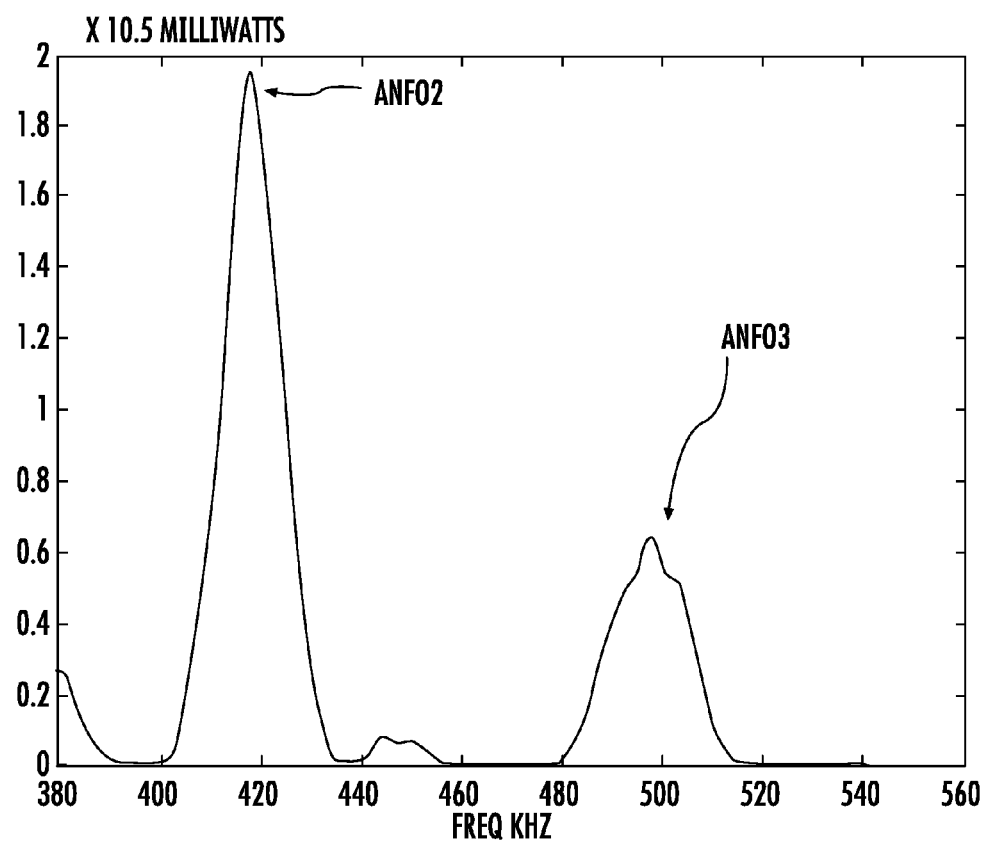
FIG. 10 illustrates resonance lines for ammonium nitrate.

In a first test, a 5.0 kilogram bucket of the commercial explosive Austinite, made is up of pure ammonium nitrate (ANFO), within the chamber during the experiment. In the band between 400-520 KHz, FIG. 10 shows two (2) resonance lines for ANFO measured near 420 KHz and 500 KHz. These two (2) ANFO resonance lines correspond closely to the second and third resonance line frequencies of ANFO identified in the published spectrum of NQR resonance lines from FIG. 9.

Figure 11A:
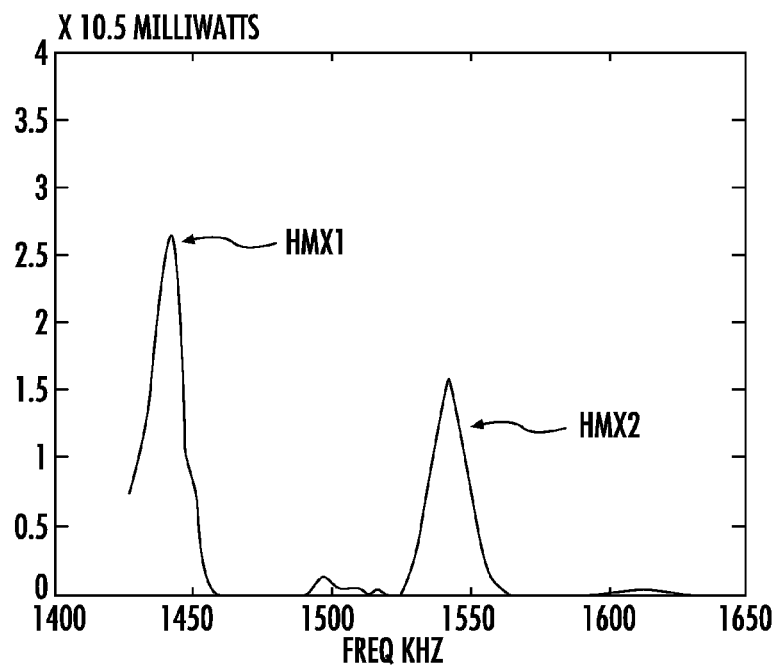
FIGS. 11(a) and 11(b) show resonance lines for HMX.

A box of 1,000.0 feet of the commercial explosive Shock Tubing containing approximately 300.0 grams of HMX was also tested. In the band between 1,425-1,600 KHz, two (2) resonance lines for HMX were measured near 1,445 KHz and 1,545 KHz as shown in FIG. 11(a) and correspond with the first and second resonance lines of HMX identified in the published spectrum of NQR resonance lines from FIG. 9.

Figure 11B:
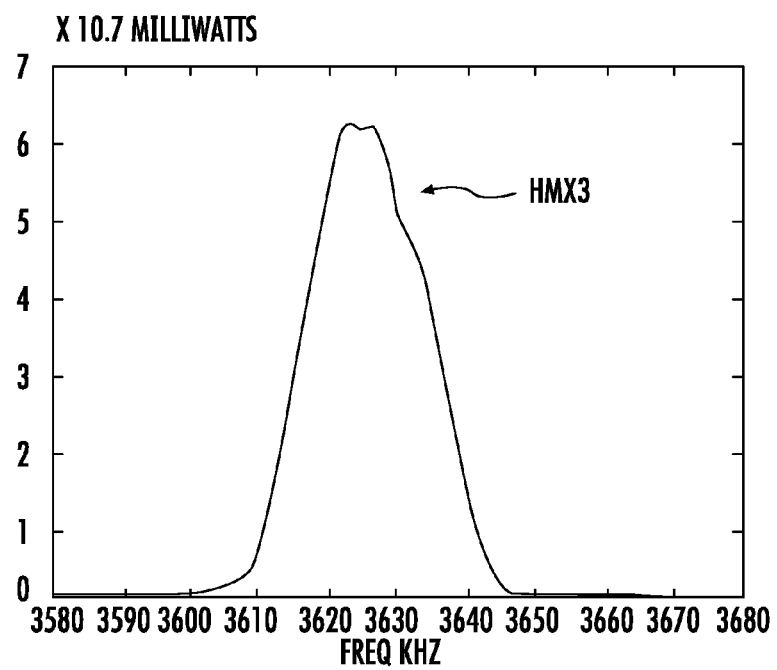

FIG. 11(b) shows the measurement of a single resonance line measured between 3,600-3,650 KHz which corresponds to the third resonance line of HMX in the published spectrum of NQR resonance lines from FIG. 9.

Figure 12A:
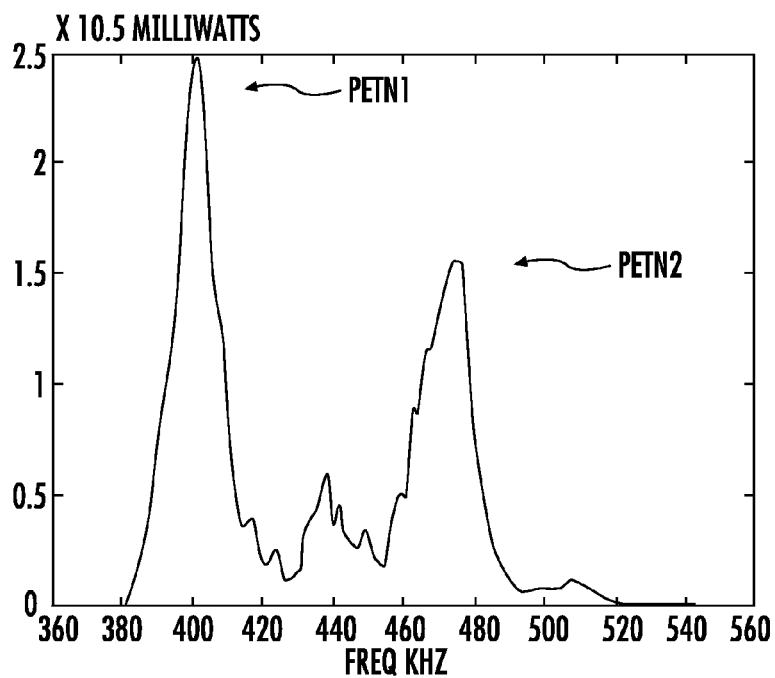
FIGS. 12(a) and 12(b) show resonance lines for PETN.
Figure 12B:
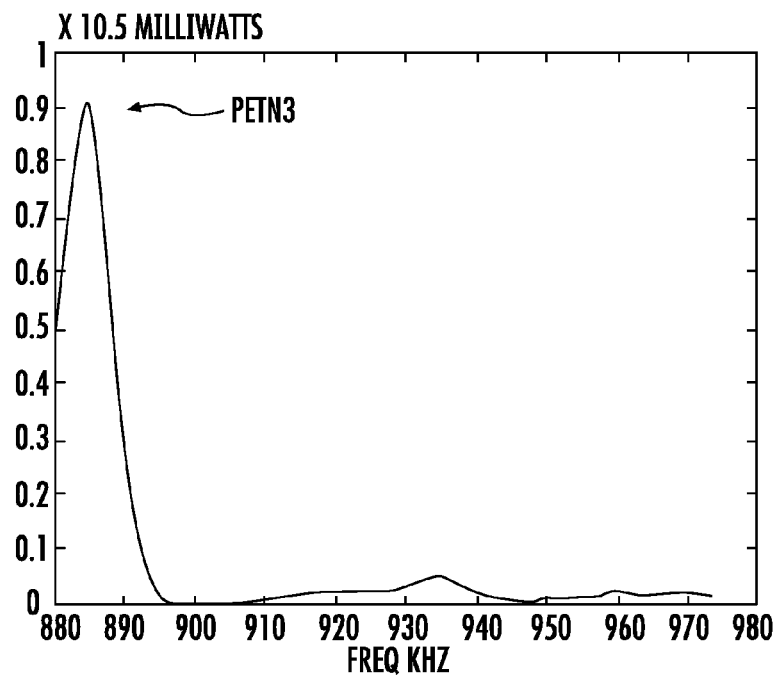

A box of 2,000.0 feet of the commercial explosive Detonating Cord containing approximately 600.0 grams of PETN was tested in the chamber. In the band between 380-520 KHz, two (2) resonance lines for PETN were measured near 400 KHz and 475 KHz as shown in FIG. 12(a) and correspond with the first and second resonance lines of PETN identified in the published spectrum of NQR resonance lines from FIG. 9. FIG. 12(b) shows the measurement of a single resonance line measured between 880-895 KHz which corresponds to the third resonance line of PETN in the published spectrum of NQR resonance lines from FIG. 9.

Figures 13A, 13B:
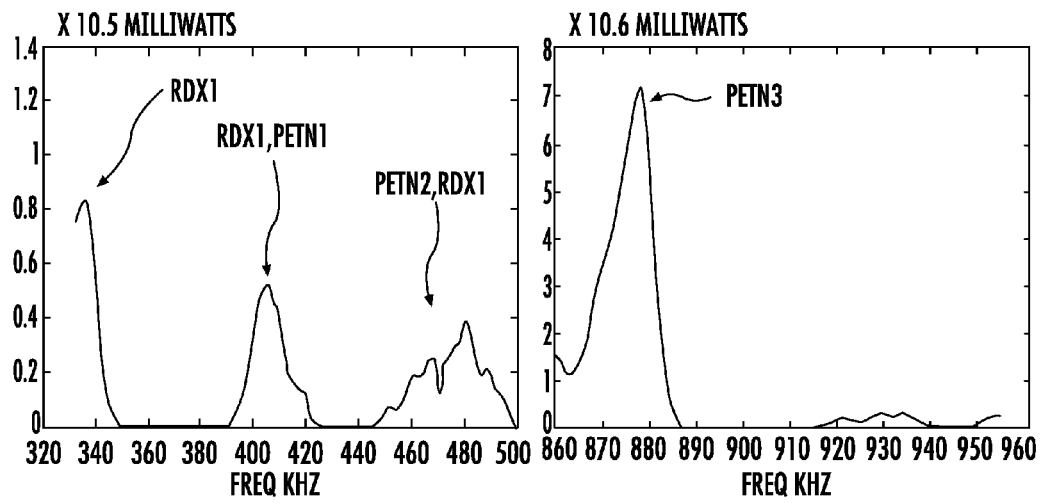
FIGS. 13(a)-13(d) show resonance responses for both PETN and RDX.
Figures 13C, 13D:
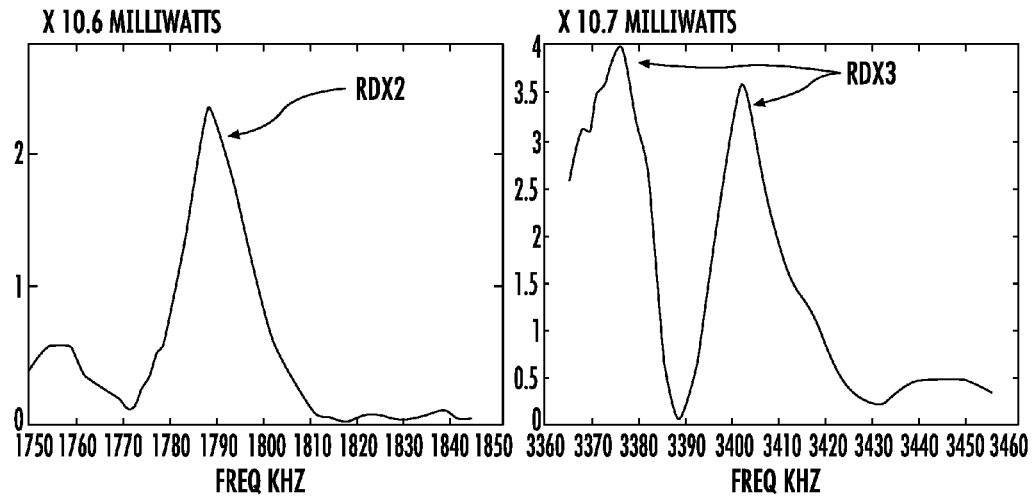

A box of seventy (70) caps of the commercial explosive Non-Electric Detonators that was also measured during the experiment. Non-Electric Detonators contain a mixture of PETN and RDX and an estimate of 226 grams of PETN and 226 grams of RDX were present in the box. FIG. 13(a) shows the measurement of a series of three (3) resonance lines between 330-500 KHz. Due to the frequencies where the resonance lines for the first group of RDX lines occur and where the first and second resonance lines of PETN occur there is overlapping of resonance lines. The first measured resonance line near 335 KHz corresponds to the first of the three resonance lines of the first group of RDX resonance lines identified in the published spectrum of NQR resonance lines from FIG. 9. The second measured resonance line near 410 KHz corresponds to the overlapped response of both the second of the three resonance lines of the first group of RDX resonance lines and the first PETN resonance line identified in the published spectrum of NQR resonance lines from FIG. 9. The third measured resonance line near 480 KHz corresponds to the overlapped response of both the third of three (3) resonance lines of the first group of RDX resonance lines and the second PETN resonance line identified in the published spectrum of NQR resonance lines from FIG. 9. FIG. 13(b) shows a measured resonance line between 860-885 KHz which corresponds to the third resonance line of PETN identified in the published spectrum of NQR resonance lines from FIG. 2. FIG. 13(c) shows a resonance line measured near 1,785 KHz which corresponds to the second resonance line of the second group of RDX resonance lines identified in the published spectrum of NQR resonance lines in FIG. 2. The two (2) measured resonance lines in FIG. 13(d) in the band between 3360-3,420 KHz correspond to the first two (2) resonance lines of the third grouping of RDX resonant lines identified in the published spectrum of NQR resonance lines in FIG. 9.

The three (3) resonance lines for PETN and the resonance lines for the three (3) is groups of RDX resonance lines were all able to be identified in this set of measurements even though PETN and RDX were mixed together.

Figure 14A:
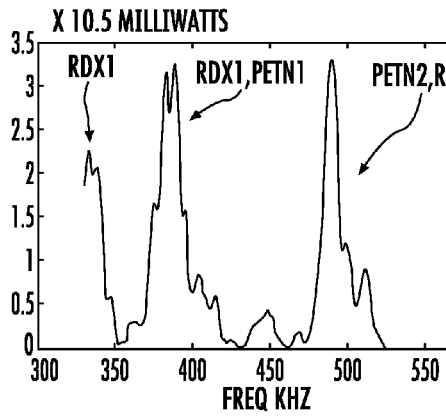
FIGS. 14(a)-14(f) show resonance lines for cast boosters containing various quantities of TNT, PETN, RDX and HMX.
Figure 14B:
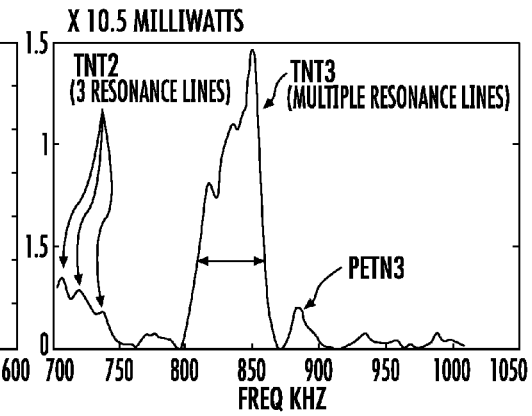
Figure 14C:
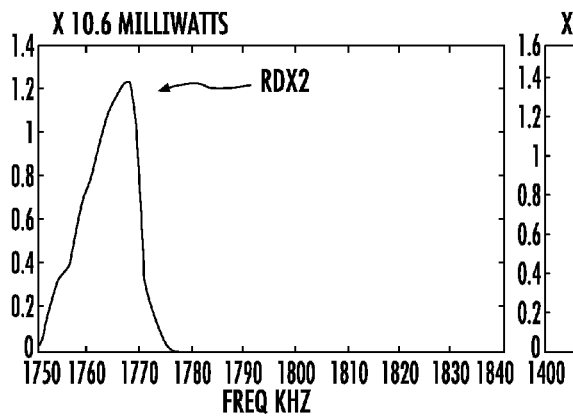
Figure 14D:
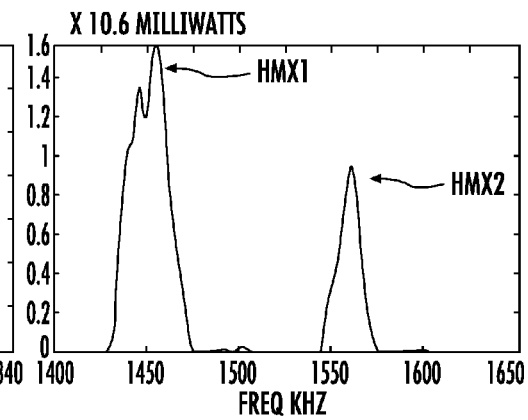
Figure 14E:
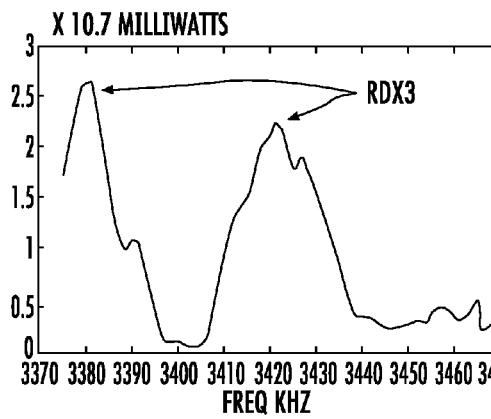
Figure 14F:
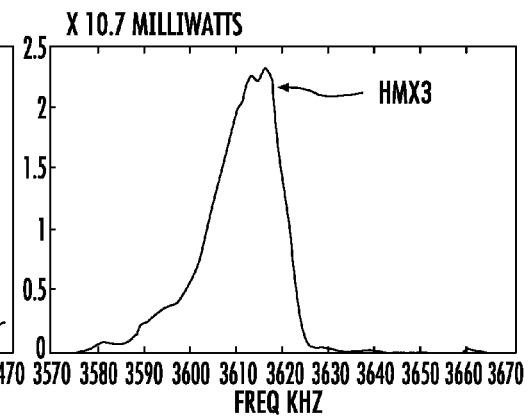

A 50.0 pound box of the commercial explosive Cast Boosters containing fifty (50) boosters were also tested. Cast Boosters contain a mixture of four (4) explosive materials: TNT, PETN, RDX and HMX and an estimate of 150.0 grams of each material was present in the box during the measurement. This estimate was made on the basis of the skin depth of the Cast Boosters. FIG. 14(a) shows the measurement of a series of three (3) resonance lines between 330-525 KHz. Like the Non-Electric Detonators, due to the frequencies where the resonance lines for the first group of RDX lines occur and where the first and second resonance lines of PETN occur there is overlapping of resonance lines for Cast Boosters. The first measured resonance line near 335 KHz corresponds to the first of the three (3) resonance lines in the first group of RDX resonance lines identified in the published spectrum of NQR resonance lines in FIG. 9. The second measured resonance line where there are two (2) peaks close to 380 KHz and 390 KHz corresponds to the overlapped response of both the second of the three (3) resonance lines of the first group of RDX resonance lines and the first PETN resonance line identified in the published spectrum of NQR resonance lines in FIG. 9. The third measured resonance line near 480 KHz corresponds to the overlapped response of both the third of three (3) resonance lines of the first group of RDX resonance lines and the second PETN resonance line identified in the published spectrum of NQR resonance lines in FIG. 9. FIG. 14(b) shows a total of three (3) resonance lines where a series of two (2) groups of measured resonance lines fall between 700-870 KHz and a single measure resonance line falls between 870-900 KHz. The first measured group of three (3) resonance lines spanning between 700-750 KHz corresponds to the second group of three (3) resonance lines of TNT identified in the published spectrum of NQR resonance lines in FIG. 9. The second group of measured resonance lines between 800-865 KHz corresponds to the third group of TNT resonance lines identified in the published spectrum of NQR resonance lines in FIG. 9, where the grouping looks like a widened resonance line rather than discrete resonance lines since the resonances in the grouping are very close in frequency. The third measured resonance line in this series near 880 KHz corresponds to the third resonance line of PETN identified in the published spectrum of NQR resonance lines in FIG. 9. FIG. 14 (c) shows a resonance line measured near 1,765 KHz which corresponds to the second resonance line of the second group of RDX resonance lines identified in the published spectrum of NQR resonance lines in FIG. 9. In the band between 1,425-1,600 KHz, two (2) resonance lines were measured near 1,445 KHz and 1,545 KHz as shown in FIG. 14(d) and correspond with the first and second resonance lines of HMX identified in the published spectrum of NQR resonance lines in FIG. 9. The (2) two measured resonance lines in FIG. 14(e) in the band between 3,375-3,440 KHz correspond to the first two (2) resonance lines of the third grouping of RDX resonant lines identified in the published spectrum of NQR resonance lines in FIG. 9. FIG. 14(f) shows the measurement of a single resonance line measured between 3,590-3,630 KHz which corresponds to the third resonance line of HMX in the published spectrum of NQR resonance lines in FIG. 9.

The three (3) resonance lines for PETN, the resonance lines for the three (3) groups of RDX resonance lines, the two (2) groups of TNT resonance lines and the three (3) resonance lines for HMX were all able to be identified in this set of measurements even when all four (4) explosive materials were mixed together.

By applying continuous wave chirp signal techniques and utilizing Rabi transition theory we have detected the NQR resonances of explosives using low power levels which are within the safe OSHA standards for humans. By utilizing Rabi transitions the nucleus oscillates between states one and two under the time dependent incident electromagnetic field and alternately absorbs energy from the incident field while emitting coherent energy via stimulated emission. This theory has been validated through both analytical means and measurement, where a system has been built and used to perform laboratory tests. The result of the theoretical formulation using the Rabi model validated the measured experimental results. This methodology was applied to demonstrate, through experimental measured results, that our system has detected the NQR signals of as little as a couple of hundred grams of explosive materials with less than 10 watts of is transmitted power. In several cases the explosives were enclosed in metal containers, but due to the low frequencies of operation the skin depth of the metal is penetrable. Through extensive electromagnetic simulation and modeling, the performance of the wideband Faraday chamber shows that a portal sized for a person to pass through will function from 330 KHz to 5 MHz. Integration of the wideband Faraday chamber with our chirp FM CW system enables direct explosives detection implemented in a walk-through portal with detection times of less than five (5) seconds. The application of this technology provides for security screening of people, detecting the NQR signal of the explosive without full-body intrusive imaging of current screening systems. The detection system is also versatile in its applicability to screening general cargo such as baggage, vehicular freight, shipping containers payloads.

What is claimed is:

1. A method for detecting presence of a substance comprising:
   disposing at least one conductive surface to define a space;
   disposing at least one conductive wire within the space adjacent the conductive surface;
   driving the conductive wire with a radio frequency chirp transmitter to create a time varying electromagnetic field within the space at a first average power level;
   detecting resulting coherent emissions at the first average power level;
   driving the conductive wire with a radio frequency chirp transmitter to create a time varying electromagnetic field within the space at a second average power level different from the first average power level;
   detecting resulting coherent emissions at the second average power level;
   comparing the coherent emissions detected at the first and second average power levels to determine properties of a substance occupied within the space;
   repeating the steps of driving the conductive wire with multiple radio frequency chips where each chirp includes one or more resonant frequencies characteristic of expected responses for certain materials of interest; and further
   feeding a radio frequency chirp signal through a plurality of amplifiers arranged in parallel;
   combining the outputs of the plurality of amplifiers prior to driving the conductive wire;
   thereby generating a series of radio frequency chirp signals with a selected one of the first or second power levels, a selected one of a sine or cosine relative phase, and a selected frequency range; and
   demultiplexing the series of radio frequency chirp signals prior to applying them to the plurality of amplifiers.

2. The method of claim 1 additionally comprising:
   adjusting for non-linearities by
      detecting coherent emissions while driving the conductive wire at the first and second average power levels while the space is known to be empty; and
      comparing the coherent emissions detected while the space is known to be empty with the coherent emissions detected with a substance occupied within the space.

3. The method of claim 1 wherein adjusting for non-linearities further comprises:
   comparing the coherent emissions detected at the first and second average power with the radio frequency chirps emitted at least at a first, second, and third frequency band, the substance known to emit a response in the first frequency band and known to not emit a response in the second and third frequency bands;
   determining a first and second difference between the first and second power levels in the second and third frequency bands; and
   using the first and second differences to estimate a correction for responses measured made in the first frequency band.

4. The method of claim 1 further comprising:
   driving the conductive wire with the radio frequency chirp transmitter through a directional coupler to create the time varying electromagnetic field within the space.

5. The method of claim 4 wherein the radio frequency transmitter produces both a sine phase chirp and a cosine phase chirp.

6. The method of claim 1 additionally comprising:
   driving the wire loop with a radio frequency transmitter to create a time varying electromagnetic field within the space at a third average power level higher than either the first or second average power levels;
   detecting resulting coherent emissions at the third power level;
   comparing the coherent emissions detected at the first and second power level to the coherent emissions detected at the third power level.

7. A system comprising:
   at least one conductive surface defining a space;
   at least one wire loop disposed within the space adjacent the conductive surface;
   a radio frequency chirp transmitter, coupled to the wire loop to emit a time varying electromagnetic field within the space at a first average power level and subsequently at a second power level;
   a detector for detecting a first set of coherent emissions resulting from the time varying field at the first average power level and at the second average power level;
   a comparator, for comparing the coherent emissions detected at the first and second average power levels to determine properties of a substance disposed within the space;
   and further comprising:
   is a plurality of amplifiers arranged in parallel to receive an output of the radio frequency chirp transmitter;
   a combiner for combining the outputs of the plurality of amplifiers, the combiner having an output coupled to the wire loop; and
   a controller for controlling the transmitter to generate a series of radio frequency chirp signals, each of the series having a selected one of the first or second average power levels, a selected one of a sine or cosine relative chirp phase, and a selected frequency range for the chirp; and
   a demultiplexer for demultiplexing the series of radio frequency chirp signals.

8. The system of claim 7 wherein:
   the radio frequency chirp further emits a time varying electromagnetic field within the space at a third average power level that is higher than either the first or second average power levels; and
   the detector further detects resulting coherent emissions at the third power level; and
   the comparator further compares the coherent emissions detected at the first and second power level to the coherent emissions detected at the third power level.

9. A system as in claim 7 further comprising:
   a processor, for comparing the coherent emissions detected as a result of the radio frequency chirp signals in at least two series emitted at two different selected average power levels to determine properties of a substance disposed within the space.

10. A system comprising:

at least one conductor or disposed within a space adjacent a conductive surface;

a chirp signal generator;

a plurality of amplifiers arranged in parallel to receive the chirp signal;

a combiner for combining the outputs of the plurality of amplifiers, the combiner having an output coupled to the at least one conductor;

a controller for controlling the chirp signal generator to generate a series of radio frequency chirp signals, each of the series having a selected average power level, a selected one of a sine or cosine relative chirp phase, and a selected frequency range for the chirp;

a coupler, for coupling the output of the combiner to the conductor to emit a time varying electromagnetic field within the space;

a detector for detecting a first set of coherent emissions resulting from the time varying field;

a processor, for comparing the coherent emissions at least to determine properties of a substance disposed within the space; and a demultiplexer, arranged to demultiplex the series of radio frequency chirp signals.

11. The system of claim 10 wherein the coupler further comprises:

a directional coupler coupled to the combiner to create the time varying electromagnetic field within the space.

12. The system of claim 10 wherein the controller further controls the chirp signal generator to emit:

multiple radio frequency chirp signals at a first and second average power level, where each chirp includes one or more resonant frequencies characteristic of expected responses for certain substances of interest.

* * * * *

UNITED STATES PATENT AND TRADEMARK OFFICE
CERTIFICATE OF CORRECTION

Page 1 of 2

PATENT NO. : 8,912,788 B2
APPLICATION NO. : 13/901765
DATED : December 16, 2014
INVENTOR(S) : John T. Apostolos et al.

It is certified that error appears in the above-identified patent and that said Letters Patent is hereby corrected as shown below:

In the specification:

Col. 2, line 33 should read:
proportional to the square of the differences in transmittal Col. 3, line 45 should read:
nances of explosives involve continuous Rabi transitions Col. 6, line 25 should read:
responses are compared 504 for each frequency that may be Col. 8, line 53 should read:
explosive Austinite, made up of pure ammonium nitrate Col. 9, line 52 should read:
lines for the three (3) groups of RDX resonance lines were Col. 11, line 2 should read:
of transmitted power. In several cases the explosives were In the claims:

Claim 7, Col. 12, line 42 should read:
a plurality of amplifiers arranged in parallel to receive an Claim 8, Col. 12, line 56 should read:
the radio frequency chirp transmitter further emits a time varying Signed and Sealed this
Seventh Day of April, 2015

Michelle K. Lee
*Director of the United States Patent and Trademark Office*

CERTIFICATE OF CORRECTION (continued)
U.S. Pat. No. 8,912,788 B2

Claim 10, Col. 13, line 5 should read:
at least one conductor disposed within a space adjacent